United States Patent [19]
Eldridge, Jr. et al.

[11] Patent Number: 5,195,538
[45] Date of Patent: Mar. 23, 1993

[54] SURGICAL INSTRUMENT TRAY

[75] Inventors: John D. Eldridge, Jr.; Mary A. Morgan, both of Newport Beach, Calif.

[73] Assignee: Devon Industries, Inc., Chatsworth, Calif.

[21] Appl. No.: 662,242

[22] Filed: Feb. 27, 1991

[51] Int. Cl.⁵ .............................................. B65D 85/24
[52] U.S. Cl. .................................... 128/849; 128/852; 206/363; 206/370; 206/438
[58] Field of Search ................ 128/849, 852; 206/363, 206/370, 350, 438

[56]  References Cited
U.S. PATENT DOCUMENTS

| | | |
|---|---|---|
| 3,201,028 | 8/1965 | Fossler et al. |
| 3,262,283 | 7/1966 | Taylor . |
| 3,456,865 | 7/1969 | Frank . |
| 3,482,567 | 12/1969 | Franklin . |
| 3,483,494 | 12/1969 | Cromie . |
| 3,503,391 | 3/1970 | Melges . |
| 3,522,800 | 8/1970 | Lesser . |
| 3,546,643 | 12/1970 | Virostek . |
| 3,654,047 | 4/1972 | Berkowitz . |
| 3,727,658 | 4/1973 | Eldridge, Jr. ........................ 206/370 |
| 3,861,521 | 1/1975 | Burtz . |
| 4,013,109 | 3/1977 | Sandel ................................ 206/370 |
| 4,051,845 | 10/1977 | Collins . |
| 4,100,684 | 7/1978 | Berger . |
| 4,169,472 | 10/1979 | Morris . |
| 4,336,806 | 6/1982 | Eldridge, Jr. . |
| 4,344,532 | 8/1982 | Eldridge, Jr. et al. ............. 206/370 |
| 4,373,629 | 2/1983 | Ulin et al. .......................... 206/350 |
| 4,485,919 | 10/1984 | Sandel . |
| 4,524,767 | 6/1985 | Glassman . |
| 4,733,806 | 3/1988 | Sloop . |
| 4,793,483 | 12/1988 | Holmes ............................... 206/363 |
| 4,886,165 | 12/1989 | Annett ................................ 206/370 |

FOREIGN PATENT DOCUMENTS 965384 4/1975 Canada .

Primary Examiner—Robert A. Hafer
Assistant Examiner—Kerry Owens
Attorney, Agent, or Firm—Knobbe, Martens, Olson & Bear

[57] ABSTRACT

A retainer and method of producing a retainer which cooperates with either a magnetic or non-magnetic surgical drape to hold instruments during surgical operations. A rectangular tray includes a wall which extends from the periphery of a base portion. The polypropylene base portion is thermally bonded to a thermoplastic rubber retainer to sandwich magnetic elements therebetween. The magnetic elements are magnetically attracted to a magnetic drape and thereby secure the retainer in any orientation with respect to the drape. The method including vacuum forming a thermoplastic shell over a tray configured mold to sandwich a magnetic element between the thermoplastic shell and a retainer.

32 Claims, 2 Drawing Sheets

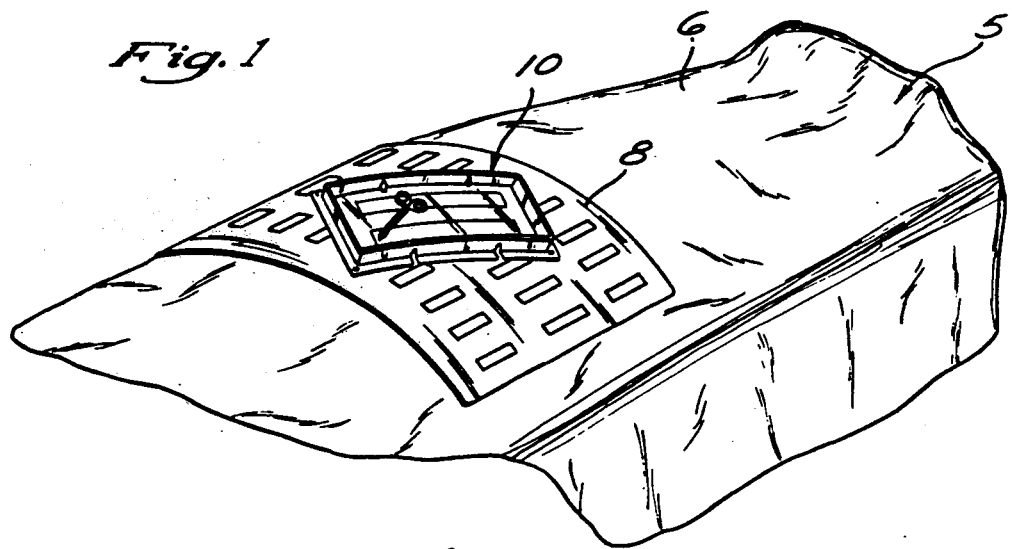
Fig. 1
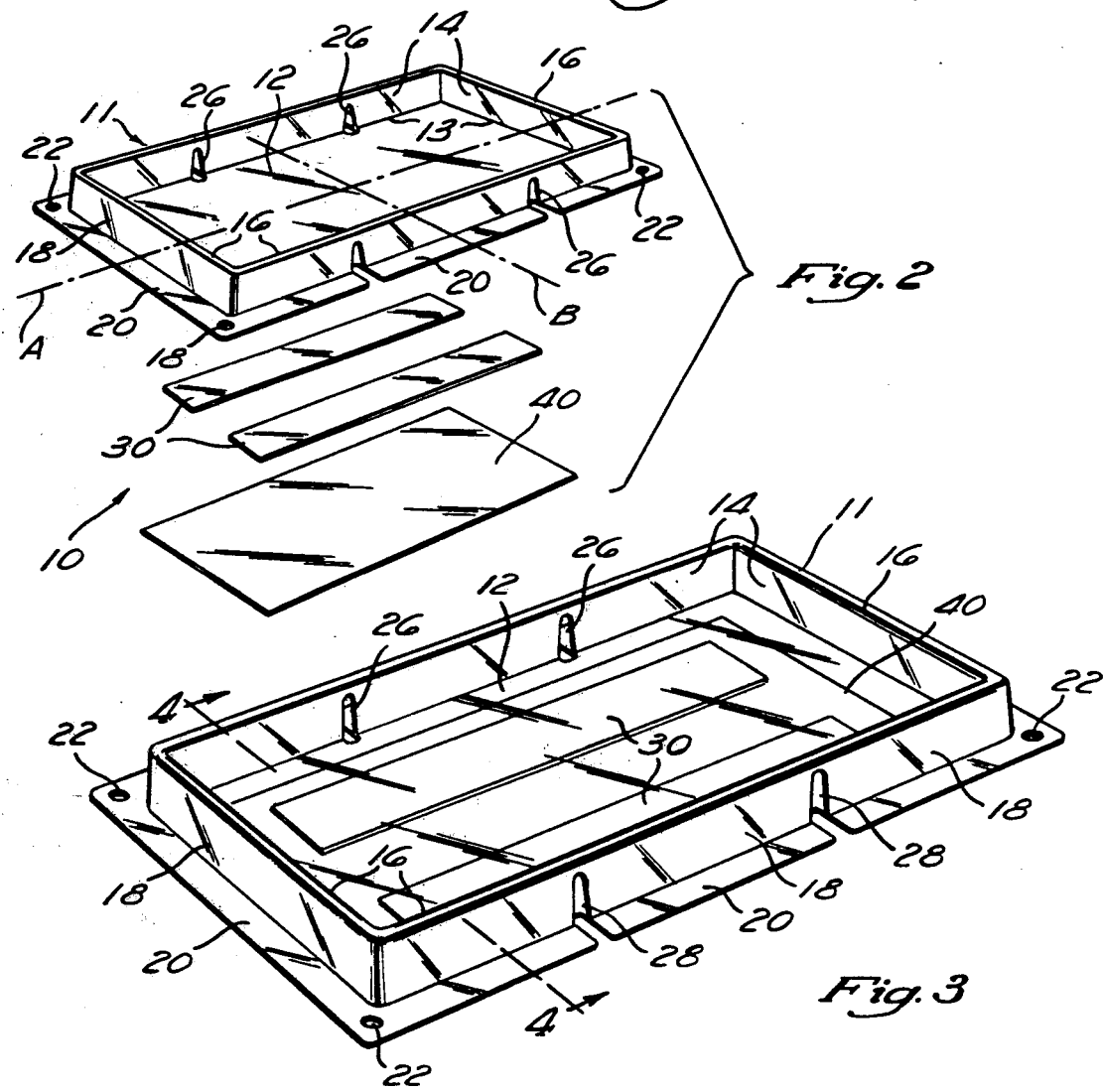
Fig. 2
Fig. 3

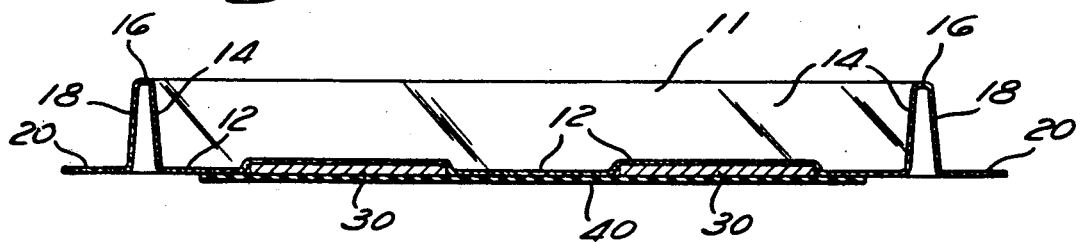
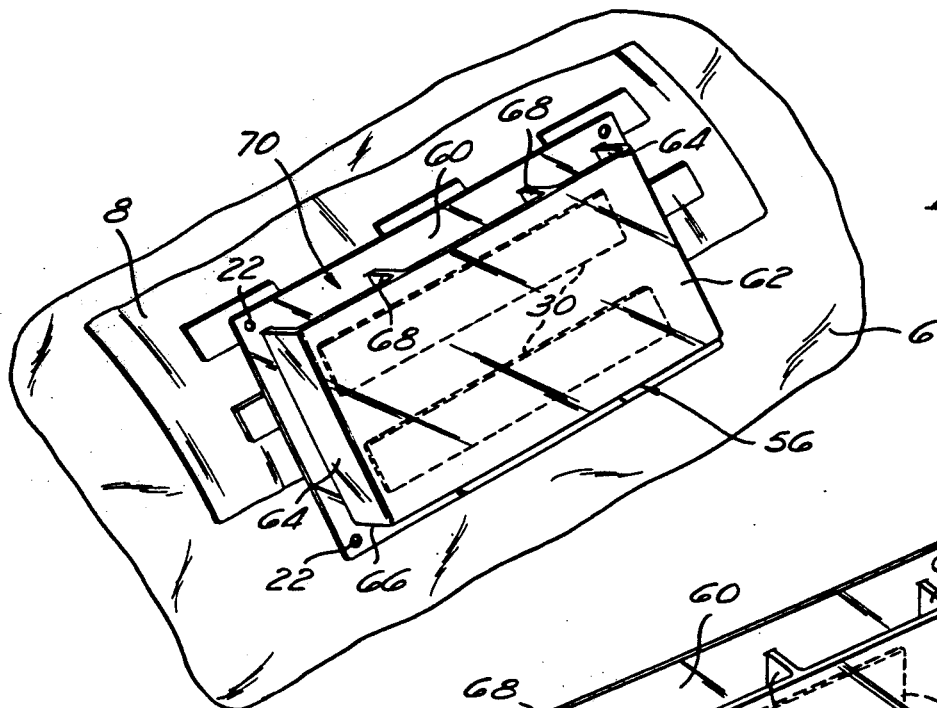
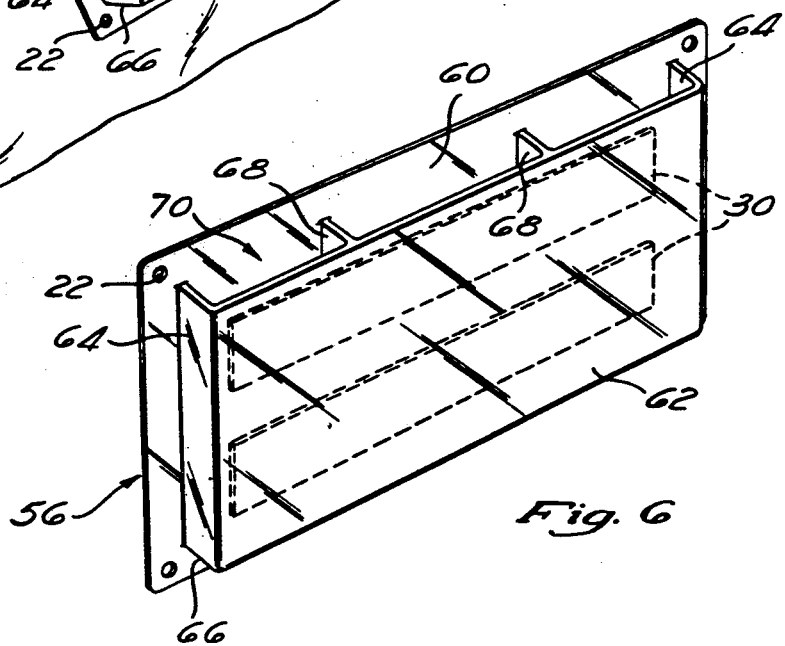

SURGICAL INSTRUMENT TRAY

This application is a division of application Ser. No. 312,135, filed Feb. 17, 1989 now U.S. Pat. No. 5,005,590.

BACKGROUND OF THE INVENTION

The present invention relates generally to the field of devices for retaining surgical instruments, and more particularly, to a plastic retainer which may cooperate with either a magnetic or non-magnetic surgical drape to retain medical instruments during surgery.

In the course of surgery, a wide variety of instruments are used. Although the surgeon may use only one or two instruments at a time, the remaining instruments must be readily available for immediate use. In addition, operating procedures require that certain instruments be discarded after just a single use. Therefore, the operating field may include sterile instruments, reuseable contaminated instruments and contaminated instruments which must be discarded. Because each category of instruments must remain separate, the operating field must accommodate a number of instrument retainers.

To accommodate the large number of instruments, sterile magnetic surgical drapes which can be laid on the patient proximal to the incision area have been developed. The magnetic drapes include a plurality of magnets sealed within the drape. Instruments can be laid on the drape by the surgeon and subsequently picked up without requiring time-consuming reaching by the surgeon. Since these drapes conform to the patient, the embedded magnets attract the instruments to the drape, thereby preventing the instruments from sliding off the drape onto the floor. See, for example, U.S. Pat. No. 3,727,658 entitled "Receiver for Surgical Implements," issued to Eldridge on Apr. 17, 1973, and U.S. Pat. No. 3,483,494 entitled "Magnetic Surgical Drape," issued to Cromie on Dec. 9, 1969. Specifically, the disclosure of U.S. Pat. No. 3,727,658 issued to Eldridge and U.S. Pat. No. 3,483,494 issued to Cromie are hereby incorporated by reference.

A major drawback of the magnetic surgical drapes is that instruments fabricated from a non-magnetizable material, such as plastic or brass, will not adhere to the drape. Further, certain magnetizable instruments are adversely effected by proximity to a magnetic field. For example, it is critical that needle clamps release a needle when desired. However, if the needle clamp or needle is exposed to a magnetic field and either becomes magnetized, then a magnetic attraction between the needle clamp and needle will prevent release of the needle at the desired time. In addition, because the instruments are retained on different areas of the drape, the placement of an instrument in the wrong area may contaminate an entire series of instruments.

In an attempt to resolve these problems, trays have been affixed to a non-magnetic drape by use of sterilized tape. However, a quantity of tape sufficient to secure the tray to the drape may not be sufficient to secure the tray when a quantity of instruments has been placed in the tray. The additional weight of the instruments may cause the tape to fail, allowing the tray and instruments to fall to the floor. Delicate and valuable instruments may be irreparably damaged by falling to the floor. Further, removal of the instruments from the surgical field requires resterilization, thereby adding to the cost of the procedure. In addition, the lightweight drape is often dislodged by an unbalanced tray affixed to the drape. Movement of the drape may cause the instruments to fall from the tray. Exposure of the tape to fluids may also cause the tape to fail. In addition, a tray affixed with tape does not provide a structure which allows for ready relocation of the tray.

An alternative approach for retaining instruments during surgery has included the use of metal trays as receptacles. However, the use of metal trays has severe drawbacks. The hardness of the metal trays may damage delicate instruments, as the instruments are placed into and slide within the tray. Further, the metal trays are non-disposable, thereby requiring substantial sterilization procedures. The necessary sterilization procedures increase the cost of using the metal trays. The cost of manufacturing the metal trays further increases the expense to the hospital. In addition, the noise of instruments contacting the base and walls of a metal traY creates a substantial distraction to the surgeon, thereby creating a risk of injury to the patient.

Therefore, a need exists for a surgical instrument tray which may cooperate with magnetic or non-magnetic surgical drapes in any orientation with respect to the drape without damaging or magnetizing instruments as they are placed in the tray. Further, the need exists for the tray to be either disposable and, therefore, inexpensive to manufacture or alternatively reusable through the established sterilization process.

SUMMARY OF THE INVENTION

The present invention provides for an inexpensive surgical instrument tray having an element therein which provides for magnetic attraction between the tray and a magnetic surgical drape. Preferably, the tray is fabricated to have a flexural rigidity which permits the tray to conform to the curvature of the operating field.

The disclosed surgical instrument tray comprises a non-magnetic shell having a base portion including a magnetic element which may cooperate with a magnetic drape, an inner wall, and preferably an outer wall having a skirt. The base portion is defined by a periphery from which the inner wall extends upwardly to join the outer wall, thereby forming a brim. In a preferred embodiment, the outer wall descends from the brim to form a skirt which is substantially coplanar with the base portion. Preferably, the skirt includes a plurality of apertures which cooperate with surgical towel clamps to secure the surgical instrument tray to a non-magnetic surgical drape.

The base portion incorporates the magnetic element which cooperates with the magnetic drape to secure the surgical instrument tray relative to the magnetic drape. Preferably, the magnetic element is comprised of galvanized steel, thereby reducing the magnetic affinity between the disclosed surgical instrument tray and the surgical instruments. However, the magnetic element may comprise a material capable of producing a magnetic field external to the magnetic element.

Preferably, the surgical instrument tray is of a substantially rectangular configuration wherein the inner wall rises from the base portion at approximately a 15° angle from vertical, and terminates at the brim. The outer wall descends from the brim to the skirt at an angle of approximately 15° from vertical. The inner and outer walls thereby form a taper such that a brim, inner and outer walls of a second tray may be received within the taper of the inner and outer walls of the first tray.

The present invention thereby provides for a surgical instrument tray which may be vertically stacked for economical transportation and efficient use of space in the operating room. In addition, the ability of the surgical instrument trays to stack allows a tray to nest over a lower tray, thereby safely enclosing contaminated instruments within the nested trays.

Further, the present invention is preferably comprised of a thermoplastic formed over a material which bonds to the thermoplastic so as to retain the magnetic elements. It is preferable that the present invention be made of thermal-formed polypropylene vacuum-drawn over a thermoplastic rubber retainer. The magnetic element is positioned so as to be sandwiched between the thermoplastic rubber retainer and the polypropylene shell. The magnetic element is oriented so as to engage the magnetic drape independent of the orientation of the surgical instrument tray relative to the magnetic drape.

In a second preferred embodiment, the surgical instrument tray may comprise a substantially rectangular volume which is oriented vertically in its operable position. The retainer includes a back wall incorporating a magnetic element, a front wall spaced from and opposed to the back wall, wherein two end walls and a bottom wall connect the front wall to the back wall, thereby forming a retainer having an aperture opposite to the bottom wall, through which instruments are received in the retainer.

BRIEF DESCRIPTION OF THE DRAWINGS

FIG. 1 is a perspective view of the first preferred embodiment of the present invention in a surgical field.

FIG. 2 is an exploded perspective view of the first preferred embodiment of the present invention.

FIG. 3 is a perspective view of the first preferred embodiment showing the notched recesses.

FIG. 4 is a cross-sectional view taken along line 4—4 of FIG. 3.

FIG. 5 is a perspective view of a second preferred embodiment of the present invention as employed in a surgical field.

FIG. 6 is a perspective view of the second preferred embodiment of the present invention.

DETAILED DESCRIPTION OF THE PREFERRED EMBODIMENT

Referring to FIG. 1, a surgical instrument tray 10 of the present invention is shown. The surgical instrument tray 10 may be used in conjunction with a magnetic 8 or non-magnetic 6 surgical drape. The magnetic drape 8 is a flexible sheet having a plurality of magnets embedded within the sheet. Specifically, U.S. Pat. No. 3,727,658 and U.S. Pat. No. 3,483,494 disclose magnetic surgical drapes of the type shown. Typically, the large non-magnetic drape 6 is placed over a patient 5 so as to cover a substantial portion of the patient 5. The magnetic drape 8 is placed over the non-magnetic drape 6 proximal to the surgical fold. The flexibility of the non-magnetic and magnetic drapes 6, 8 allows the drapes to conform to the contour of the patient 5. The flexural rigidity of surgical instrument tray 10 permits the surgical instrument tray to substantially conform to the contour of the magnetic and non-magnetic drapes 6, 8. The surgical instrument tray 10 cooperates with the magnetic drape 8 to provide a receptacle for the necessary surgical instruments. Alternatively, the surgical instrument tray 10 may engage the non-magnetic drape 6 by means of surgical towel clamps (not shown). Therefore, the surgical instrument tray 10 may be used in conjunction with either the magnetic drape 8 or the non-magnetic drape 6.

As shown in FIG. 2, the surgical instrument tray 10 includes a rectangular shell 11, a retainer 40 and magnetic elements 30. The shell 11 may comprise a thermoplastic material. It is advantageous that the thermoplastic material exhibit a resistance to high temperatures such as those incurred in the autoclave process. Although the shell 11 may be formed from any suitable thermoplastic material, it is desirable that the shell 11 is comprised of polypropylene. The shell 11 includes a substantially planar base portion 12, defined by a rectangular periphery 13 from which an inner wall 14 rises. Preferably, the inner wall 14 completely encircles the periphery 13 to form a continuous wall. The inner wall 14 joins an outer wall 18 to form a brim 16 such that the brim 16 is disposed above the plane of the base portion 12. The outer wall 18 descends from the brim 16 to form a skirt 20, which is substantially coplanar with the base portion 12. The skirt 20 includes a plurality of clamp apertures 22 which cooperate with surgical towel clamps well known in the art. The use of the surgical towel clamps permits the tray 10 to be secured to a non-magnetic drape.

Preferably, the base portion 12, inner wall 14, brim 16, outer wall 18 and skirt 20 are integrally formed from thermoformed polypropylene. The polypropylene may be vacuum drawn to obtain the desired configuration by means of a thermomolding process well-known in the art.

As shown in FIG. 2, magnetic elements 30 are disposed beneath the base portion 12, sandwiched between the retainer 40 and the base portion 12. The retainer 40 may comprise any material which will bond to the shell 11. Preferably, the retainer 40 is comprised of a thermoplastic material. It is advantageous that the retainer 40 comprise a thermoplastic rubber. However, if a disposable surgical instrument tray 10 is desired, the retainer 40 may comprise a porous or non-porous thermoplastic foam. While the thermoplastic foam is advantageous in the thermoforming process, the foam permits penetration of water to the magnetic elements 30 during the sterilization process. This exposure of the magnetic elements 30 to moisture results in oxidation of the magnetic elements 30, thereby rendering the surgical instrument tray 10 unusable after the first use. Advantageously, the retainer 12 is a thermoplastic rubber, which bonds to the polypropylene shell 11 during the thermoforming process. The thermoplastic rubber prevents migration of moisture to the magnetic elements during the sterilization process, thereby providing for a reusable surgical instrument retainer.

The magnetic elements 30 may be of any material actuated by magnetic attraction. Preferably, the magnetic elements 30 are a galvanized steel. The magnetic elements 30 comprising a galvanized steel provide a resistance to corrosion and an increased magnetic attraction to the magnetic drape. In addition, the galvanized steel shields instruments placed within the tray from the magnetizing effect of the magnets embedded in the magnetic drape 8. The magnetic elements 30 have a thickness which permits flexure of the magnetic elements 30. Preferably, the magnetic elements have a thickness of approximately 0.015 inches. However, the magnetic elements may alternatively comprise a material capable of producing a magnetic field external to itself.

The magnetic elements 30 may be configured as rectangular strips such that a portion of the retainer 40 extends beyond each edge of the magnetic element 30. The portion of the retainer 40 which is not covered by the magnetic elements 30 provides a surface which will bond with the polypropylene shell 11 during the thermoforming process to secure the magnetic elements 30 between the retainer 40 and the polypropylene shell 11. Although not shown, the magnetic elements may be directly affixed to the shell 11 by a variety of means well known in the art, such as adhesives and mechanical fasteners. Affixing the magnetic elements directly to the shell 11 would remove the necessity of the retainer 40.

As shown in FIG. 4, the inner wall 14 and the outer wall 18 diverge from their junction at the brim 16. In the first preferred embodiment, the inner wall 14 and the outer wall 18 are each inclined approximately 15° from a perpendicular orientation with respect to the plane of the base portion 12. The inner wall 14 and the outer wall 18 diverge from the brim 16, thereby forming a taper between the inner wall 14 and the outer wall 18. The taper of the inner wall 14 and the outer wall 18 permits a brim 16, inner wall 14 and outer wall 18 of a second surgical instrument tray to be received within the taper. Vertical nesting of multiple trays reduces the shipping and storage volume of the present invention. In addition, the vertical nesting permits the enclosure of contaminated instruments between nested surgical retainer trays, thereby reducing the risk of exposure to the contaminated instruments.

As shown in FIG. 2, in the first preferred embodiment, the shell 11 has a rectangular configuration, wherein the dimensions of the base portion 12 are defined by a major axis A perpendicular to a minor axis B such that the major axis A is greater than the minor axis B.

As shown in FIG. 3, the inner walls 14, which are parallel to the major axis A, may contain notched recesses 26. The recesses 26 intersect the base portion 12 and extend substantially the height of the inner wall 14. The outer wall 18 includes notched recesses 28 opposite each recess 26 of the inner wall 14. The recesses 28 extend through the skirt 20 and extend substantially the height of the outer wall 18. Although the shell 11 exhibits a flexural rigidity, the recesses 26, 28 permit the shell 11 to bend along its major axis A, thereby allowing the shell 11 to more closely conform to the magnetic drape, independently of the orientation of the shell 11 relative to the contour of the underlying drape and the patient 5.

Referring to the first preferred embodiment as shown in FIGS. 1–4, the magnetic elements 30 are configured as rectangles. The rectangular magnetic elements 30 are oriented such that the long sides of the magnetic elements 30 are parallel to the major axis A of the base portion 12. As shown in FIG. 4, the magnetic elements 30 are oriented so that a portion of the retainer 40 is bonded to the base portion 12 proximal to each edge of the magnetic element 30. The magnetic elements 30 are thereby exposed to only the base portion 12 and the retainer 40. Because there is no exposure of the magnetic elements 30 to the environment, there is a reduced susceptibility of the magnetic elements 30 to oxidization. In addition to their orientation, the magnetic elements 30 are sized so that at least one magnetic element 30 engages the embedded magnets of the magnetic drape 8 independent of the orientation of the surgical instrument tray 10 with respect to the magnetic drape 8.

Specifically, in the preferred embodiment, the major axis A of the base portion 12 has a length of approximately eight inches, and the minor axis B has a length of approximately four inches. Preferably, each magnetic element 30 is approximately one inch wide and six inches long. In the preferred embodiment, the magnetic elements 30 are disposed parallel to the major axis A such that the six inch edges of the magnetic elements 30 are approximately two-thirds of an inch from each other and from the periphery 13. The one inch edges of the magnetic elements 30 are preferably parallel to the minor axis B and are approximately one inch from the periphery 13.

The magnetic drape is preferably configured to provide parallel rows of magnets, wherein each magnet is approximately 1.5 inches long and 0.5 inches wide. The magnets within each row are parallel such that the 1.5 inch dimension of the magnets are parallel and the magnets are approximately 1.75 inches from center line to center line. The rows of magnets are parallel, wherein the distance between the row center lines is approximately 2.75 inches.

Therefore, in the preferred embodiment, if the surgical instrument tray 10 is oriented parallel with a row of magnets, a magnetic element 30 will engage at least three magnets with the given row. If the surgical instrument tray 10 is perpendicular to the rows of magnets, a magnetic element 30 will engage at least three magnets. Therefore, the surgical instrument tray 10 will operably engage the magnetic drape 8 even though one of the magnetic elements 30 is not engaged by any magnets. When both magnetic elements 30 are within the array of magnets, a plurality of magnets are engaged by the magnetic elements 30, independent of the orientation of the surgical instrument tray 10 with respect to the magnetic drape 8.

Although the preferred embodiment has been described in terms of specific dimensions, the magnetic elements 30 may be sized and configured in alternative forms which permit engagement of the surgical instrument tray 10 by the magnetic drape 8 independent of the orientation of the surgical instrument tray relative to the magnetic drape 8.

Further, the plurality of clamp apertures 22 permits the engagement of the surgical instrument tray 10 with a non-magnetic drape 6 independent of the orientation of the surgical instrument tray 10 with respect to the non-magnetic drape 6.

In the thermoforming process, the magnetic elements 30 are placed on the retainer 40 so that a portion of the retainer 40 extends beyond the periphery of each magnetic element. The shell 11 is then vacuum-drawn on a mold placed over the retainer 40 and magnetic element 30. The heat of the vacuum forming process bonds the retainer 40 to the shell 11, thereby securing the magnetic elements 30 between the retainer 40 and the shell 11. However, as will be appreciated by one skilled in the art, the magnetic elements 30 may be bonded to the shell 11 by a variety of means, including adhesives and mechanical fasteners.

Referring to FIGS. 5 and 6, a second preferred embodiment of the present invention is shown. The second preferred embodiment includes a pouch or receptacle 56 which may depend in a vertical orientation from a magnetic or non-magnetic drape to retain instruments during surgery. The receptacle 56 may be of a thermoplastic material which exhibits a resistance to high temperatures. Preferably, the receptacle 56 is formed from polypropylene and includes a rectangular front wall 62 having an end wall 64 extending perpendicularly from each end edge of the front wall 62. The end walls 64 intersect a back wall 60 which is substantially parallel to the front wall 62. A bottom wall 66 intersects the front wall 62, the back wall 66 and the end walls 64 to form a receptacle for surgical instruments. An aperture 70 is formed opposite the bottom wall 66, through which instruments pass into the receptacle 56. The receptacle 56 may include ribs 68, between the front wall 62 and the back wall 60. The ribs 68 provide for individual compartments within the receptacle 56 in which instruments are retained.

The back wall 60 is thermally bonded to a retainer 40 to sandwich a magnetic element 30 between the retainer 40 and the back wall 60. However, the magnetic elements 30 may be affixed to back wall by means well known in the art such as adhesives and mechanical fasteners. As in the first preferred embodiment, the magnetic elements 30 may be actuated by magnetic attraction or alternatively, capable of producing an external magnetic field. Preferably, the magnetic elements 30 of the second preferred embodiment comprise galvanized steel which provides resistance to corrosion while providing a magnetic affinity to the magnetic drape 10. As in the first preferred embodiment, the retainer 40 may comprise a thermoplastic material. Preferably, the retainer 40 is a thermoplastic rubber which bonds to polypropylene during the thermoforming process as well known in the art. Preferably, in the second preferred embodiment the magnetic elements 30 comprise rectangular elements which are substantially parallel to the aperture 70. In this configuration a single magnetic element 30 may magnetically cooperate with the magnetic drape 8 to affix the receptacle 56 to the drape 8. In addition, both magnetic elements 30 may cooperate with the magnetic drape 8 to secure the receptacle 56 to the drape 8 in a substantially vertical orientation. However, the magnetic elements 30 are not limited to a rectangular configuration disposed parallel to the aperture 70, the magnetic elements 30 need only be disposed to ensure sufficient cooperation with the magnetic drape 8 to secure the receptacle 56 to the magnetic drape 8.

Although the present invention has been described in terms of particular embodiments, it is not limited to these embodiments. Alternative embodiments and modifications which would still be encompassed by the invention may be made by those skilled in the art, particularly in light of the foregoing teachings. Alternative embodiments, modifications or equivalents may be included within the spirit and scope of the invention, as defined by the claims.

It is claimed:

1. A surgical instrument retainer, comprising:
   a non-magnetic shell including:
   a base portion defined by a periphery, said base portion incorporating a magnetic element disposed within said periphery;
   an inner wall projecting from said periphery and terminating at a brim, said inner wall having a notched recess; and
   an outer wall depending from said brim, said outer wall having a notched recess opposite said notched recess of said inner wall, wherein said notched recess of said inner wall and said notched recess of said outer wall provide increased flexure of said surgical instrument retainer.

2. A surgical instrument retainer comprising:
   a non-magnetic back wall incorporating a magnetic element;
   a front wall spaced from and opposed from said back wall, said spacing forming an aperture through which instruments are passed;
   a bottom wall wherein said bottom wall includes a plurality of apertures which allow the passage of fluid; and
   two end walls extending from said front wall to said back wall, said end walls maintaining the spacing between said front wall and said back wall, said space and said aperture cooperating to allow access to the interior of said surgical instrument retainer.

3. A surgical instrument retainer, comprising:
   a non-magnetic shell including:
   a base portion defined by a periphery;
   a magnetic element; and
   a wall projecting from said periphery, said wall terminating at a distance from said base portion, wherein said wall includes at least one notched recess, wherein said notched recess provides increased flexure of said surgical instrument retainer.

4. The surgical instrument retainer of claim 1, wherein said inner wall encircles said periphery to form a continuous wall.

5. The surgical instrument retainer of claim 1, wherein said outer wall further comprises a skirt projecting from said outer wall, and wherein said skirt is substantially coplanar with said base portion.

6. The surgical instrument retainer of claim 1, wherein said skirt is integrally formed with said outer wall.

7. The surgical instrument retainer of claim 1, wherein said non-magnetic shell comprises a thermoplastic.

8. The surgical instrument retainer of claim 1, wherein said non-magnetic shell comprises polypropylene.

9. The surgical instrument retainer of claim 1, wherein said magnetic element is capable of producing a magnetic field external to said magnetic element.

10. The surgical instrument retainer of claim 1, wherein said base portion includes a plurality of magnetic elements.

11. The surgical instrument retainer of claim 1, further comprising:
    a plurality of apertures in said skirt for securing said skirt to a surgical drape by means of a surgical towel clamp.

12. The surgical instrument retainer of claim 1, wherein said inner wall is inclined less than 20° from vertical and said outer wall is inclined less than 20° from vertical.

13. The surgical instrument retainer of claim 1, wherein said inner wall is configured to receive a base portion of a second surgical instrument retainer.

14. The surgical instrument retainer of claim 1, further comprising:
    a cover affixed to said base portion wherein said magnetic element is disposed between said base portion and said cover.

15. The surgical instrument retainer of claim 2, wherein said back wall is of a substantially rectangular configuration.

16. A surgical instrument retainer adapted for use with a magnetic surgical drape, said instrument retainer comprising:
- a non-magnetic base portion defined by a periphery, said base portion having an upper surface and a lower surface;
- a wall extending from said periphery and terminating at a distance from said base portion upper surface, said wall and base portion adapted such that metallic and non-metallic surgical instruments can be received and stored within said retainer and freely removed from said retainer; and
- a metallic element permanently fixed and secured to said base portion lower surface, said metallic element adapted to be magnetically attracted to said magnetic surgical drape when said drape is draped over a patient during surgical operations, said retainer being adapted to be releasably secured to said drape during operations to allow said instruments, which are not magnetically attracted to either said drape or said metallic element, to be retained and stored adjacent said patient in said retainer.

17. The retainer of claim 16, wherein said metallic element is made of galvanized steel.

18. The retainer of claim 16, wherein said metallic element is approximately 0.015 inches thick.

19. The surgical instrument retainer of claim 16, wherein said metallic element has a thickness of less than 0.025 inches.

20. The surgical instrument retainer of claim 16, wherein said metallic element is capable of producing a magnetic field external to said metallic element.

21. The surgical instrument retainer of claim 16, wherein said non-magnetic base is comprised of a thermoplastic material.

22. The surgical instrument retainer of claim 16, wherein said non-magnetic base is comprised of polypropylene.

23. A surgical instrument retainer, comprising:
- a base portion defined by a periphery;
- a wall projecting from said periphery, wherein said wall terminates at a distance from said base portion, said retainer being adapted such that surgical instruments can be received and stored in said retainer and easily removed during surgical operations; and
- a metallic element permanently fixed and secured to said base portion, adapted such that said element is actuated by magnetic attraction to a magnetic surgical drape, which is draped over a patient during surgical operations, said retainer being adapted to be releasably secured to said drape to allow said instruments to be retained and stored in said retainer adjacent said patient during said operations.

24. The retainer of claim 23, wherein said element is adapted such that said surgical instruments in said retainer are not in magnetic attraction with said element or retainer.

25. The surgical instrument retainer of claim 23, wherein said metallic element is comprised of a galvanized steel.

26. The surgical instrument retainer of claim 23, further comprising a plurality of metallic elements.

27. The surgical instrument retainer of claim 23, wherein said element is no thicker than 0.025 inches.

28. The surgical instrument retainer of claim 23, wherein said metallic element is secured to the bottom of said base portion.

29. The surgical instrument retainer of claim 23, wherein said base portion and said wall are comprised of an integrally formed thermoplastic.

30. The surgical instrument retainer of claim 23, wherein said base portion and said wall are comprised of an integrally formed polypropylene.

31. The surgical instrument retainer of claim 23, wherein said wall is inclined less than 20° from vertical.

32. The surgical instrument retainer of claim 23, wherein said wall is configured to receive a base portion of a second surgical instrument retainer.

* * * * *